United States Patent [19]

Göltner et al.

[11] 4,257,419
[45] Mar. 24, 1981

[54] SUCTION-ASSISTED HEMORRHOID LIGATOR

[75] Inventors: Ewald Göltner, Fulda; Karl-Heinz Lurz, Künzell, both of Fed. Rep. of Germany; Gerhard Schneider, Ålta, Sweden

[73] Assignee: Mo och Domsjo Aktiebolag, Ornskoldsvik, Sweden

[21] Appl. No.: 969,613

[22] Filed: Dec. 14, 1978

[51] Int. Cl.³ .................... A61B 17/00; A61B 17/12
[52] U.S. Cl. .................... 128/303 A; 128/326
[58] Field of Search .................... 128/318, 326, 303 A

[56] References Cited

U.S. PATENT DOCUMENTS

| | | | |
|---|---|---|---|
| 2,942,604 | 6/1960 | Granlee, Jr. | 128/326 |
| 3,173,414 | 3/1965 | Guillant | 128/318 |
| 3,361,382 | 1/1968 | Converse | 128/326 |
| 3,382,873 | 5/1968 | Banich et al. | 128/326 |
| 3,760,810 | 9/1973 | Van Hoorn | 128/326 |
| 3,856,018 | 12/1974 | Perisse et al. | 128/326 |
| 4,085,743 | 4/1978 | Yoon | 128/303 A |
| 4,103,680 | 8/1978 | Yoon | 128/303 A |

FOREIGN PATENT DOCUMENTS 2308846 8/1973 Fed. Rep. of Germany .......... 128/326

Primary Examiner—Robert W. Michell
Assistant Examiner—C. W. Shedd

[57] ABSTRACT

A ligator is provided for pinching off hemorrhoids and similar body tissues, comprising, in combination, a tubular housing; a suction tube fixedly mounted on the housing; and an actuator sleeve slidably mounted for reciprocable movement within the housing along the suction tube; a suction cup defining an open suction cavity facing outwardly and fixedly attached to and in flow communication with the suction tube for sucking a hemorrhoid into the suction cavity, the suction cup having means for receiving an elastic ring about the periphery of the open suction cavity; and means for ejecting said ring from the cup and onto the body portion link of a hemorrhoid sucked into the suction cavity and projecting from the cavity; said ejecting means being movable by reciprocation of the actuator tube between nonactuated passive and actuated ring-ejecting positions.

11 Claims, 7 Drawing Figures

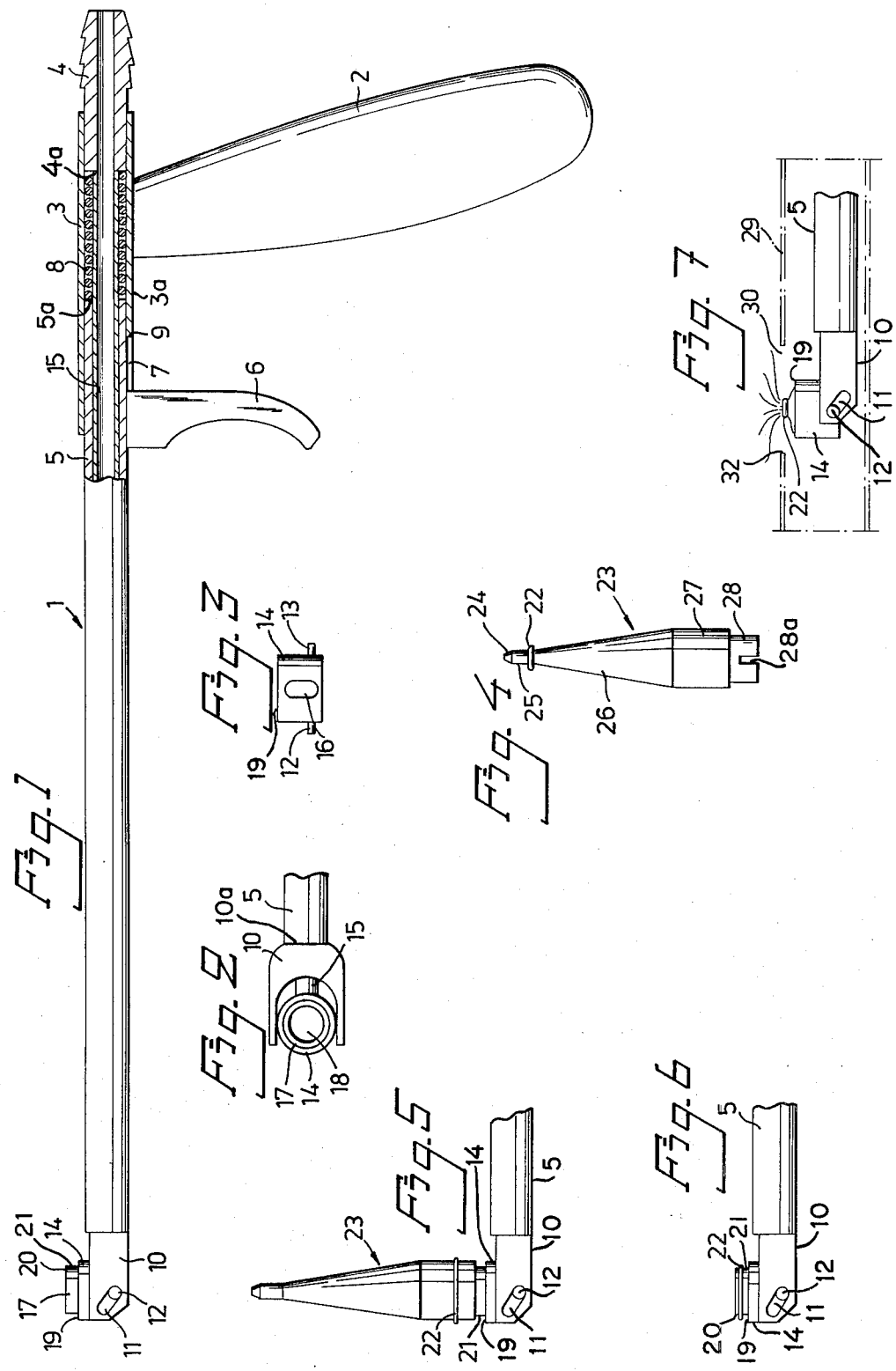

SUCTION-ASSISTED HEMORRHOID LIGATOR

A common method for destroying hemorrhoids without surgery pinches off the hemorrhoid from the body in a manner such that the hemorrhoid has its blood supply cut off, dies, and is sloughed off by the body. To do this, an extremely small elastic band or ring is placed around the body link to the hemorrhoid. This requires that the ring be stretched out sufficiently to be passed over the hemorrhoid, and then released, and this is quite difficult to do manually.

A typical manual operation suitable for excrescent hemorrhoids is carried out with a proctoscope, through which a forceps can be inserted to grasp the hemorrhoid, and pull it through the stretched elastic band or ring. It is however difficult to place the band or ring around the hemorrhoid in this way, and the method cannot really be used for surface hemorrhoids, which do not project any significant distance from the body. Accordingly, various types of devices have been designed to do this mechanically.

U.S. Pat. No. 3,382,873 to Banich and Jordan, patented May 14, 1968, provides a surgical instrument for placing a rubber band around a hemorrhoid, comprising a first cylindrical member having a longitudinal axis; a second cylindrical member movably positioned with the first cylindrical member to move from a first to a second position; in the first position, the second member having a lip portion extending beyond the first cylindrical member, and in the second position the lip portion is within the first member; a support member affixed to the first cylindrical member; an actuator arm affixed to the second cylindrical member; a bearing surface in the support member; a guide member on the actuator arm; and a means including a trigger for biasing the actuator arm and the guide member against the support member and the bearing surface and for moving the second cylindrical member along the axis to remove a rubber band on the lip.

With this construction, it is asserted, it is possible for the operating surgeon to take a pair of forceps and after the instrument has been placed about a hemorrhoid to reach through the hollow inner cylinder 11 and to grasp the hemorrhoid and pull it through the cylinder. At the time it is withdrawn sufficiently the surgeon merely pulls the trigger 31, and the rubber band 40 is placed about the hemorrhoid. It is then left there and since the blood supply has been cut off from the hemorrhoid it will die of its own lack of oxygen and food and will drop off. The area is closed over by scar tissue and the result is that the patient has a minimum of inconvenience and has a minimum of recovery time from this procedure.

U.S. Pat. No. 3,760,810 to Van Hoorn, patented Sept. 25, 1973, provides a device comprising two tubes mounted for relative sliding movement, one inside the other, the inner tube protruding at the front of the outer tube. A grip member is connected to one of said two tubes and has actuating means to produce a relative displacement of the outer tube forwardly relative to the inner tube. The outer tube and/or the inner tube has a greater length than the depth of the cavity up to the structure to be ligated, so that it constitutes an endoscope. In the device shown in FIG. 15, suction is applied in order to draw the hemorrhoid into the tube 2.

In the instrument of FIG. 15 the tubes 1 and 2 are extended toward the back by means of a sleeve 62 locked or threaded into the back part 15 of tube 2. This sleeve 62 is closed by a transparent screen 63 made for example of glass. A joint 64 may be provided to ensure a good seal between the screen 63 and the sleeve 62.

The sleeve 62 is perforated to form a lateral opening 65 and a bent connecting tube 66 is attached to the periphery of this opening. The tube 66 is adapted to be connected to a flexible tube 67 which communicates with a vacuum pump.

When the instrument of FIG. 15 is lodged in a cavity containing a structure to be ligated, for example the anal canal, the transparent screen permits an observation of this cavity and orienting the instrument carefully so that the extremity 14 of tube 2 is placed in the vicinity of a structure 34 to be ligated. The vacuum pump is then actuated which results in pulling the structure 43 into tube 2.

This device however, because the opening into the cavity is axial, is difficult to maneuver in a manner so that the hemorrhoid, particularly a surface hemorrhoid, can be drawn into the tube for pinching off. While the device of U.S. Pat. No. 3,382,873 is better suited for this purpose, there is of course no way of applying suction in that design. Moreover, there is no way in either device of preventing unwarranted extension of the hemorrhoid during the operation. The hemorrhoid may be carried into the tube 2 together with part of the rectum wall, for example, so that pinching off of the hemorrhoid at the right place becomes impossible.

In accordance with the invention, a hemorrhoid ligator is provided, designed to draw a hemorrhoid into a suction cup, and with the opening into the suction cup facing outwardly, and to one side, preferably at a 90° angle, but suitably at from 45° to 90° to the longitudinal axis of the ligator, so as to pinch off not only excrescent hemorrhoids, but also surface hemorrhoids.

The ligator in accordance with the invention comprises, in combination, a tubular housing; a suction tube fixedly mounted on the housing; and an actuator sleeve slidably mounted for reciprocable movement within the housing along the suction tube; a suction cup defining an open suction cavity having a volume approximating the size of the hemorrhoid to be pinched off and facing outwardly and to one side, fixedly attached to and in flow communication with the suction tube for sucking a hemorrhoid into the suction cavity, the suction cup having means for receiving an elastic ring about the periphery of the open suction cavity; and means for ejecting said ring from the cup and onto the body portion link of a hemorrhoid sucked into the suction cavity and projecting from the cavity; said ejecting means being movable by reciprocation of the actuator tube between nonactuated passive and actuated ring-ejection positions.

The suction cup has a limited volume, to accommodate a hemorrhoid, but no more. It thus has predetermined bottom and side dimensions selected according to the hemorrhoid sizes to be accommodated therein, and exclude adjacent body parts such as the rectum wall, as well as preventing unnecessary extension of the hemorrhoid itself.

A preferred embodiment of the invention is shown in the drawings in which:

FIG. 1 is a side view, partly in section, of a hemorrhoid ligator in accordance with the invention;

FIG. 2 is a detailed top view of the suction head and associated components of the ligator of FIG. 1;

FIG. 3 is a detailed side view of the elastic ring ejector of the ligator of FIG. 1;

FIG. 4 is a detailed view of an element for positioning a ring at the periphery of the suction cup on the ring-carrying member of the ligator of FIG. 1;

FIG. 5 shows the device of FIG. 4 attached to the ring-carrying member, in position for transfer of a ring to that member;

FIG. 6 shows the ring after transfer to the ring-carrying member of the ligator of FIG. 1; and FIG. 7 shows the ligator of FIG. 1 in use to suck in and pinch off a hemorrhoid in the anal passage of the body.

The hemorrhoid ligator 1 of FIG. 1 is preferably of stainless steel or inert plastic such as polycarbonate, polyamide, polytetrafluoroethylene, or polypropylene, and has a handle 2 on which there is fixedly mounted a tubular housing 3. Into the rear end of the housing 3 is fixedly attached in a press-fit a hose coupling 4, to which there is attached a hose (not shown) extending from a suction source to the ligator, for application of a suction to produce a partial vacuum to the suction cup 17, 18 of from about 0.3 to about 0.4 kp/cm². The coupling is fixedly attached to the housing, and if a press-fit be inadequate, soldering, welding, adhesive bonding, or mechanical means such as screws or a bayonet joint can be used instead.

Within the tubular housing 3 is slidably mounted an actuator sleeve 5, and within the sleeve 5 and serving as a guide for reciprocation thereof is a suction tube 15, fixed immovably to the housing 3 by attachment to the coupling 4 at the inner end 4a thereof. Such attachment can be the same as for the coupling 4 to housing 3. All of these parts are coaxial and concentric, and preferably are cylindrical, as shown, but the suction tube can of course be arranged beside the sleeve 5, although less desirably, for space reasons.

The lower face 3a of the housing 3 carries an open slot 7. A trigger 6 that is fixedly attached to the actuator sleeve 5 slides along the slot 7 between an inward limiting position defined by the end 9 of the slot 7 and/or pegs 12, 13 in slots 11 (see below), and an outwardly limiting position (shown in FIG. 1) defined by the pegs 12, 13 in slots 11.

A compression spring 8 captured between the inner ends 5a of the sleeve 5 and 4a of the coupling 4 biases the actuator sleeve 5 towards the normally outermost position shown in FIG. 1, but the sleeve 5 can be drawn inwardly against the biasing force of the spring by squeezing the trigger 6 towards the handle 2 to the innermost position where the trigger 6 abuts the end of the slot 9, for actuation of the ejector for the ring carried by the device, as will presently be seen.

At the opposite outer end of the actuator sleeve 5 is fixed a bifurcated support 10 (best seen in FIG. 2) attached at the base end 10a to the sleeve 5 for reciprocable movement therewith, and with an inclined groove 11 in each bifurcation (see FIG. 1). The grooves 11 capture pegs 12, 13 of the ring ejector 14 (best seen in FIG. 3), which is shown in FIG. 2 mounted in the support 10. The ejector 14 has an elongated slot 16 therethrough, through which passes the outer end of the suction tube 15. The slot 16 is elongated in the shape shown so as to be movable up and down with respect to the suction tube between the two limiting positions of the pegs 12, 13 of the ring ejector at the lower end or the upper end of the slots 11.

With the sleeve 5 extended, the ring ejector 14 is in its lowermost position at the inner and lower end of slots 11 as seen in FIG. 1, but it can be brought to the uppermost position by pressing the trigger 6 towards handle 2, to the end 9 of the slot 7, which draws the ejector 14 up to the other end of the slots 11.

As noted above, the pegs 12, 13 prevent sleeve 5 from moving out from housing 3 under the biasing force of spring 8.

Fixedly mounted at the end of the suction tube 15 is a suction cup 17, over the outer periphery 21 of which slides the ring ejector 14. The suction tube 15 enters the cup 17 at the side of the base of the suction cavity 18, but it can also enter at the bottom or a corner of the cavity. Consequently, suction can be drawn in the cavity 18 by application of suction to the tube 15 via the coupling 4 and attached hose and suction pump (not shown). The suction cup 17 is cylindrical, and the bottom of the suction cavity 18 can be either planar or concave or convex.

It now will be apparent that inasmuch as the suction cup 17 is fixed to the suction tube 15, inward movement of the sleeve 5 along the outer periphery of the suction tube 15 compels the ring ejector 14 to move upwardly towards the end of the cup 17 along the peripheral surface 21 as the pegs 12, 13 ride along the slots 11.

As seen in FIG. 1, in the nonactuated or passive position of the ring ejector 14, the portion 20, 21 of the suction cup 17 projects beyond the end of the ring ejector. In this position, the surfaces 19,21 serve as a support for an elastic band or ring placed over the suction cup 17. If however the ring ejector 14 be moved upwardly by pulling the trigger 6 inwardly, then the ring carried on the surfaces 19, 21 is ejected and driven off the end 20 of suction cup 17 when the surface 19 of the ejector reaches the end of the cup 17.

An elastic ring is placed over the end 20 onto the periphery 21 of suction cup 17 against the ledge 19 using the device 23 shown in FIGS. 4 and 5. This device has a conical tip 24 of a diameter less than that of the smallest elastic ring that is to be placed over a hemorrhoid. Such a ring is shown in FIG. 4 as 22, in position over the tip 24, and at rest against the conical expander surface 26, which which links the tip 24 to the cylindrical portion 27. The portion 27 is of greater outer diameter than the peripheral outer diameter at 21 of the suction cup 17. Extending from the cylindrical part 27 is a resilient support 28, sized to fit within cup 17 in cavity 18, with two slots 28a to improve resiliency and ensure a tight fit in the cavity 18 when the device is put in position for transfer of a ring over the end 20 onto the surfaces 19, 21, as shown in FIG. 5. Thus, the outer diameter of the portion 28 fits in a tight press-fit in the cavity 18 of suction cup 17.

After the elastic ring has been placed over the tip 24, and rolled up and over the conical surface 26, and thereby stretched to the diameter of the cylindrical part 27, the ring is expanded to larger than the outer diameter of the suction cup 17, and consequently the ring can be rolled off the part 27 onto the peripheral surface 21 of the suction cup, down against the ledge 19, or near to it, into the position shown in FIG. 6. The ligator is then loaded, ready for use.

When the ligator is placed over a hemorrhoid and the hemorrhoid is sucked into the suction cavity 18 with the body link projecting therefrom the ring 22 can readily be ejected by manipulating the trigger 6, moving the ejector 14 outwardly, and pushing the ring off the suction cup 17 onto the body link portion of the hemorrhoid. This operation is illustrated in FIG. 7, showing the ligator in position in the anus or rectum.

The ligator is inserted within a proctoscope 29, with a window 30 through which the hemorrhoid to be pinched off is observed. After it has been determined which hemorrhoid is to be pinched off, the ligator is inserted into the tube 29, and so oriented that the suction cavity 18 is in position over the hemorrhoid. Since the suction head is at an angle of approximately 90° to the longitudinal axis of the device, the suction cavity is readily brought into position over the hemorrhoid by simple rotational and axial movement along the tube 29.

After the suction cavity 18 has been placed over the hemorrhoid, the face of the suction cup 17 is moved into contact with the wall of the anus or rectum, and suction then applied. Partial vacuum is drawn in the suction cavity 18, and as a result the hemorrhoid is drawn into the suction cavity. The body link connection between the hemorrhoid and of the body lies just outside the suction cavity. The trigger 6 is then pulled inwardly towards the handle 2, as a result of which the ring ejector 14, as its pegs 12, 13 travel along the track of the grooves 11, is moved outwardly along the surface 21 of suction cup 17, pushing the ring along as it does so, and finally ejecting the ring from the cup. As soon as the ring is no longer held expanded, and in its position over the body link, as it contracts to its normal size, it pinches off the hemorrhoid, in the manner shown in FIG. 7. With the hemorrhoid thus pinched off, it will in due course die, and slough off.

It will be apparent that the device is useful to pinch off not only hemorrhoids but any type of body deformity or lesion susceptible of being destroyed in this way.

Having regard to the foregoing disclosure, the following is claimed as inventive and patentable embodiments thereof:

1. A ligator for pinching off hemorrhoids and similar body tissues at a body link portion thereof, comprising, in combination, a tubular housing; a suction tube fixedly mounted on the housing; and an actuator sleeve slidably mounted for reciprocable movement within the housing along the suction tube; a suction cup defining an open suction cavity having a volume approximating the size of the hemorrhoid to be pinched off and facing outwardly and to one side, fixedly attached to and in flow communication with the suction tube, for sucking a hemorrhoid into the suction cavity; the suction cup having means for receiving an elastic ring about the periphery of the open suction cavity; and means for ejecting said ring from the cup and onto the body link portion of a hemorrhoid sucked into the suction cavity and projecting from the cavity; said ejecting means being movable by reciprocation of the actuator tube between nonactuated passive and actuated ring-ejecting positions; the outer end of the actuator sleeve having fixed thereto a bifurcated support attached at its base end to the sleeve for reciprocable movement therewith, and with an inclined slot in each bifurcation, the slots capturing projections on the external periphery of the ejecting means slidably mounting the ejector on the support.

2. A ligator according to claim 1 in which the opening into the suction cup faces outwardly, and to one side, at an angle from about 45° to about 90° to the longitudinal axis of the ligator.

3. A ligator according to claim 1 in which the housing, tube, sleeve and suction cup are of a material selected from the group consisting of stainless steel and inert plastic.

4. A ligator according to claim 1 in which the rear end of the housing is fixedly attached in a press-fit to a hose coupling, to which there is attached a hose extending from a suction source to the ligator, for application of a suction to produce a partial vacuum in the suction cup.

5. A ligator according to claim 1 in which the tubular housing, sleeve and suction tube are coaxial and concentric.

6. A ligator according to claim 5 in which the tubular housing, sleeve and suction tube are cylindrical.

7. A ligator according to claim 1 in which a lower face of the housing carries an open slot, and a trigger fixedly attached to the actuator sleeve, and slides along the slot between an inward limiting position defined by one end of the slot, and an outwardly limiting position defined by a stop.

8. A ligator according to claim 7 in which a compression spring is captured between the inner ends of the sleeve and a suction coupling, biasing the actuator sleeve towards the normally outermost position in the slot, the sleeve being drawn inwardly against the biasing force of the spring by squeezing the trigger towards the handle.

9. A ligator according to claim 1 in which the ejecting means and the suction cup are cylindrical and concentric, the ejecting means being outside the suction cup, and movable up and down along the outside of the suction cup between the two limiting positions of the projections on the ejecting means at the lower end and the upper end of the slots, the ejecting means being brought to the uppermost position by pressing the trigger towards the handle.

10. A ligator according to claim 9 in which in the nonactuated position of the ejecting means the suction cup projects beyond the end of the ejecting means as the external surface serving as a support for an elastic band placed over the suction cup, but when the ejecting means is moved upwardly by the trigger, then the band carried on the surface is ejected and driven off the end of the suction cup when the end of the ejecting means reaches the end of the cup.

11. A ligator according to claim 1 in which the suction cup is cylindrical, and the bottom of the suction cavity is one of planar, concave and convex.

* * * * *